United States Patent [19]

Hodakowski

[11] Patent Number: 5,439,683
[45] Date of Patent: Aug. 8, 1995

[54] PADDY RICE TREATMENT

[75] Inventor: Leonard E. Hodakowski, Raleigh, N.C.

[73] Assignee: Rhone-Poulenc Inc., Research Triangle Park, N.C.

[21] Appl. No.: 122,987

[22] Filed: Sep. 20, 1993

Related U.S. Application Data

[63] Continuation-in-part of Ser. No. 959,020, Oct. 9, 1992, abandoned.

[51] Int. Cl.⁶ .................. A01N 25/00; A01N 25/02; A01N 25/04
[52] U.S. Cl. ............................ 424/408; 206/524.7; 424/405; 424/406; 424/409; 424/412
[58] Field of Search ............... 424/408, 405, 406, 409, 424/412; 206/524.7, 521; 428/35.5; 514/801, 944; 71/DIG. 1

[56] References Cited

U.S. PATENT DOCUMENTS

| | | | |
|---|---|---|---|
| 3,171,779 | 3/1965 | McCoy et al. | 424/622 |
| 3,253,984 | 5/1966 | Seymour et al. | 514/772.4 |
| 3,253,985 | 5/1966 | Seymour et al. | 514/772.4 |
| 3,885,950 | 5/1975 | Ehrig et al. | 504/312 |
| 3,892,905 | 7/1975 | Albert | 428/220 |
| 4,058,067 | 11/1977 | Wright et al. | 111/100 |
| 4,546,108 | 10/1985 | Rout et al. | 514/464 |
| 4,692,494 | 8/1987 | Sonenstein | 525/57 |
| 4,885,105 | 12/1989 | Yang et al. | 252/90 |
| 4,983,390 | 1/1991 | Levy | 424/404 |
| 5,080,226 | 1/1992 | Hodakowski et al. | 206/205 |
| 5,139,152 | 8/1992 | Hodakowski et al. | 206/524.7 |
| 5,341,932 | 8/1994 | Chen et al. | 206/524.7 |
| 5,394,990 | 3/1995 | Edwards et al. | 206/524.7 |
| 5,395,616 | 3/1995 | Edwards et al. | 424/405 |
| 5,395,617 | 3/1995 | Edwards et al. | 424/405 |

FOREIGN PATENT DOCUMENTS

| | | |
|---|---|---|
| 4-334302 | 11/1992 | Japan . |
| 5-078203 | 3/1993 | Japan . |
| 5-078207 | 3/1993 | Japan . |
| 5-339103 | 12/1993 | Japan . |
| 6-024904 | 2/1994 | Japan . |
| 922317 | 3/1963 | United Kingdom . |

Primary Examiner—Melvyn I. Marquis
Assistant Examiner—Robert H. Harrison
Attorney, Agent, or Firm—Morgan & Finnegan

[57] ABSTRACT

A method of treatment of a paddy whereby a plant protecting effective amount of a plant protecting composition, with the water soluble envelope containing it, is dropped in different locus of the water of a paddy where the rice plants are growing, this plant protecting composition being in a viscous or sticky fluid form, such as a liquid or a gel, which is able to spread rapidly and uniformly along the surface of the water of the paddy and coat the rice plant of insect in response to changes in the water level.

20 Claims, No Drawings

PADDY RICE TREATMENT

This application is a continuation-in-part of U.S. Ser. No. 07/959,020, filed Oct. 9, 1992, now abandoned.

BACKGROUND OF THE INVENTION

I. Field of the Invention

The invention relates to new methods for treatment of paddy rice. More specifically, it relates to a method of treating paddy rice, wherein a water soluble package containing a viscous or sticky fluid or gel plant protecting agent is placed in the rice paddy such that the agent spreads to form a uniform film, which can coat the rice plants in response to water levels changes in the rice paddy.

II. Discussion of the Related Art

It is well known that paddy rice, as well as most other crops in the world, is commonly infested with many pests, such as insects and weeds.

There are many difficulties in treating paddies in order to control weeds or insects because of the unusual wetland growing conditions used to raise paddy rice in addition to those difficulties found with most crops.

First of all, there are the classical problems of all pesticidal compositions having a pesticidal active ingredient. These products should be applied to the crops in a safe manner and need to be applied in a timely and efficient manner for the composition to have its greatest effect.

The application of an effective amount of these products in a safe manner on crops means that an effective amount of active ingredient is provided to the plant while a minimum amount of the said active ingredient is applied or remains elsewhere, either in the environment, on the application tools or machinery, or onto the persons who are handling these products. A safe manner to apply the active ingredient includes reduced worker exposure to these products, safety for the environment, including spills, and minimized container disposal issues.

The application of these products in an efficient manner means that an effective amount of active ingredient is provided to the plant which needs it, in order to save it from the pests. That is to say, the amount of insecticides afforded to the plant should be large enough to kill the insects attacking or going to attack the plant during a substantial time frame. It also means the amount of herbicides afforded to the plant should be large enough to kill the weeds or to slow down or prohibit the growth of weeds competing with the crop, and this effect should remain during a substantial time frame. Still another requirement is that a uniform or balanced amount of active ingredient should be applied to the plants in order that phytotoxicity and efficacy are well coordinated.

Regarding the paddies, one common method of applying pesticides is to introduce the mixture on the water of the paddy, so that the active ingredient is spread out and dispersed on the surface of the water, and reaches the rice plant so as to have its efficacy directly on the plant at the interface of the water surface and plant.

Rice paddies are fields that can be flooded with water and usually bordered by an elevated dry area or other such edge area. In order to have the active ingredient spread out in a uniform manner, the most practical manner currently used is where the farmer, walks through the flooded area of the paddy, with his feet immersed in water, as he introduces the active ingredient in the water near him. Unfortunately and obviously, a major drawback of this method is to have the farmer, through his feet, permanently in contact with a liquid (the water of the paddy) containing the pesticide.

One solution to the above problems is described in Japanese Patent No. 563-30281 to Nihon Kayaku K.K., published Jul. 29, 1985 and granted on Jun. 17, 1988. The method described in this patent involves use of a powder and dry granules of active ingredient in water soluble packaging. The granules initially sink to the bottom then eventually float on the surface and dissolve in the water. While they avoid the need to walk in the flooded area, granules deliver active at other than the surface, are relatively slow to dissolve and disperse on the surface of the water, are expensive to make and still represent a dusting problem during manufacture, do not coat the surface of the water evenly and may only afford protection at the interface between the film on the water surface and the plant and do not coat the plant under changing water levels in the rice paddy.

There are many methods of treatment of paddy by all kind of agrochemicals, either liquid or solid, but there is a need to find better methods to increase simultaneously the safety for people who are handling the active ingredient and the efficacy of the active ingredient for the plant, i.e. rice plant.

SUMMARY OF THE INVENTION

An object of the instant invention is to provide a new and safe method of treatment of paddies against pests.

Another object of the instant invention is to provide a new method of treatment for paddies which is simultaneously safe for the workers and efficient for the crop.

Another object of the instant invention is to provide an inexpensive and easy method of treatment for rice paddies.

Other objects of the instant invention will better appear in the description which follows.

Another object of the instant invention is to provide a safe and easy method to protect paddies against insecticidal attacks, said method being better able, not only to spread on the surface of water of paddies, but also to join or coat the stems of plants and the insects walking thereon or going to walk thereon.

Another object of the instant invention is to provide a safe and easy method to protect paddies against insecticidal attacks, said method being better able, not only to spread on the surface of water of paddies, and to join the stems of plants but also to remain on or to coat to such stems.

Another object of the instant invention is to provide a safe and easy method to protect paddies against insecticidal attacks, said method being better able, not only to spread on the surface of water of paddies and to join or coat the insects walking on or going to walk on the stems of plants, but also to remain on or to coat such insects.

Another object of the instant invention is to provide a safe and easy method to protect paddies against insecticidal attacks, said method being better able to form less waste water, especially less waste water containing insecticides.

Another object of the instant invention is to provide a safe and easy method to protect paddies against insecticidal attacks, said method being better able to lose less insecticides in the water of paddies.

It has been found that one or more of these objects can be met by the method of treatment of paddy of the instant invention.

The invention provides a new method of treatment of a rice paddy whereby a plant protecting composition in a water soluble envelope is dropped onto a paddy where the rice plants are growing or will grow, this plant protecting composition being a viscous or sticky fluid or gel and able to spread rapidly and uniformly along the surface of the water of the paddy and coat the rice plants in response to changes in water level.

According to a preferred feature of the invention, a gel composition is used.

According to another feature of the invention, the size of the bag and the concentration of active ingredient (plant protecting) is determined so as to be able to protect an area large enough so that there is no need to walk through the field to treat it.

DETAILED DESCRIPTION OF THE INVENTION

More precisely, the invention provides a new method of treatment of a paddy utilizing an effective amount of a plant protecting composition, with the water soluble envelope containing it, the method comprising positioning in different loci of the water of a paddy where the rice plants are growing, the plant protecting composition being in the form of a viscous or sticking fluid or gel, which is able to spread rapidly and uniformly along the surface of the water of the paddy and coat the rice plant when the water level is lowered or raised in the field.

By positioning, it is meant to drop, throw, place or the like in the water from a position outside the water, preferably the dry bank.

By plant protecting composition, it is meant a composition comprising an active ingredient which may have a plant protection action, such as a plant growth regulator, herbicide, a pesticide or the like. This pesticide may be an insecticide or a fungicide or a nematicide or a miticide or a molluscicide. Herbicides are considered as plant protecting in the sense that they protect the crop by killing the weeds.

By viscous liquid or gel is meant a liquid plant protection composition having a Brookfield viscosity sufficient such that the viscosity aids the active in coating the plant on response to water level changes. This would be around at least 200 cps up to as much as 50,000 cps but will vary from compound to compound. By sticky it is meant that composition which contains, or is itself a sticker, that is the plant protecting composition will adhere or coat the plant in response to changes in water level. This is normally accomplished by choosing a liquid solvent which has a higher affinity for organic materials than for water. Once the liquid or gel has formed a film on the surface of the water, changes in the level of water will cause the liquid or gel to coat the rice plants. This coating will give protection from insects which actually exists or move about on the plant and come in contact with the coating by walking or landing thereon.

Although all plant protecting agents are contemplated in this invention, nevertheless, insecticides and insecticidal compositions are especially appropriate and beneficial for rice growers. Thus the method of the invention is especially effective against insects which are moving or traveling along the stem of the plant, up and down, such as the rice water weevil, rice stem borer, grass leaf roller, rice leaf beetle, brown plant hopper and the like.

The plant protecting composition in the water soluble envelope is called hereafter a plant protecting unit.

The water soluble envelope may be of any type of enveloping system. Preferably it is a bag.

The envelope is generally made of a water soluble polymeric material in the form of a film, and this film constitutes the wall of the bag. Polymeric material which can be used in the invention are polyvinyl alcohol; cellulosic materials such as methyl or ethyl cellulose; polyalkylene oxides. A preferred material is the polyvinyl alcohol, which is advantageously totally or partially hydrolyzed or alcoholyzed polyvinyl acetate. The hydrolysis or alcoholysis rate of polyvinyl acetate in the invention is generally between about 70 and about 99% (new co-polymers get close to 100% hydrolysis. All these materials should be cold water soluble (cold means, here, less than 35° C.).

The thickness of the wall of the envelope can be great enough so that it dissolves in the water of the paddy at the desired rate. Thus the thickness is generally comprised between 1 mm and 10 micrometer. Preferably, the thickness is in the range from 10 to 150 micrometer. As newer films get developed, strength may be improved to go to thinner films. It will be desirable to use the thinnest film possible.

In order to protect the whole paddy which is to be treated, more than one envelope may be dropped into the paddy water. They are dropped in different loci so that the different surfaces which are reached by the spreading of the composition contained in one envelope are joined and formed to cover the surface of the whole paddy with as little overlap as possible. Much of this can be accomplished by making the envelope of a size such that the amount of active ingredient is appropriate for the paddy size.

In order to have the plant protecting composition spreading rapidly and uniformly and/or coating adhering or sticking or acting on the stems, further various modes of practicing the invention have also being found.

According to another feature of the instant invention, a method of treatment of paddy, as already presented, comprises further the use of a plant protecting composition which has one or more of the following characteristics.

The active ingredient, that is to say the plant protecting agent, preferably has a low water solubility. Generally solubility is less than 5% (w/w), and a solubility less than 2% is preferred. It is preferred that the active ingredient has a better solubility in the solvent of the composition than in water, so that it prefers to spread with the composition on the water rather than in the water towards the ground. Generally, the ratio of solubility in the solvent/solubility in water is more than 5, preferably more than 10. It is preferred that the active ingredient, that is to say the plant protecting agent, is in a solubilized or dispersed form. The plant protection composition is enclosed in a water soluble envelope, or preferably a bag, which is preferably able to float on the surface of the water.

It is especially preferred that in order for the plant protecting composition to form a film, it must float on water. Its specific gravity is thus preferably less than 1 g/cm$^3$, and still more preferably in the range from 0.7 to 0.98 g/cm$^3$. Specific gravity can be >1 and sink, but the material inside bag should eventually float to the surface.

The composition can also include, as an aid to the spreading, a water immiscible solvent having a specific gravity less than the specific gravity of the water of the paddy (that means generally less than 1 g/cm³). It can also comprise a cosolvent; the purpose of this cosolvent is generally to adapt the solubility and dispensability of the active ingredient in the solvent; some solvents like vegetable oils might be chosen for other beneficial properties they have and not have the best solubilizing or wetting ability; the cosolvent is the remedy to this problem.

One other optional ingredient for the plant protecting composition comprises a highly surface active agent. The surface active agent of the plant protecting composition is mainly a wetting agent having spreading properties (wetting/spreader). In order to assess whether a wetting spreader is suitable according to the invention, the following test is carried out: 1-2 drops of material in 3½ inch dish of water and looked to see what spread the best.

The plant protecting composition optionally comprises a sticker to adhere the active ingredient to the rice plant; a sticker is a material that helps adhere or coat the active ingredient to plant stem in a rice paddy having an affinity for organics relatively higher than that of water; vegetable oils which may be used as solvents are also appropriate stickers, especially cottonseed oil, soybean seed oil, corn oil, rapeseed oil, sunflower seed oil, coconut oil; hydrocarbons such as terpenes, pinene are also suitable. Hydrocarbons that are useful are those which are insoluble in water (<2% by weight), are compatible or can be made compatible with the pesticidally active ingredient, and can have their surface tension lowered (i.e., this causes rapid spreading on the water surface) by the addition of a surface active agent. The hydrocarbon solvent should have a density of a 1 g/cc so that it will float on the surface of the water rather than sink and be diluted by the water in the rice paddy. Terpenes are useful hydrocarbon sticking agents for once they adhere to a surface, they tend to react with the sunlight and polymerize on the surface of the plant which makes it more difficult for it to be washed off as the height of the paddy changes throughout the season.

The size of one bag or envelope, amounts and concentrations of ingredients in the composition contained in the bag or envelope are chosen so as to fit to an area of 100 square meter (plus or minus 10% of paddy field, The preferred size of bags used to contain the liquid or gel is in the range of 10 to 1500 ml, most preferably in the range of 10 to 500 mi. There may be needs to go bigger on sloping fields where bags are placed at the top of the field.

According to another feature of the instant invention, better adhesion of the plant protecting agent and composition is obtained when the flooded field is adjusted either artificially or by natural means such as evaporation. Thus, the invention is also directed to a method of treatment of a paddy as already defined which comprises a further optional step (after dropping the envelopes in the paddy and alley, the composition to spread on the surface) of lowering the water level in the paddy.

A particular feature of the invention is a method as already described whereby one water soluble envelope containing a plant protecting composition is dropped or thrown into a sector of the flooded paddy field, the said sector, with the other similar sectors, constituting the whole flooded paddy field. For example, it is particularly convenient and efficient to walk around the paddy field on the dry areas and to drop one envelope per square sector on a rectangular paddy field, two sectors being as long as the paddy field is wide.

Another preferred feature of the instant invention is a method which comprises application of plant protecting unit wherein the plant protecting composition is not flowing through pinholes and such as its Tg(phi) (as hereafter defined) is less than or equal to 1.5, for example through use of a gel.

Many types of insecticides may be used in the invention, for example carbaryl, Thiodicarb, Ebufos, Carbosulfan, Amitraz, Vamidothion, Ethion, Triazophos, Propoxur, Phosalone, Parathion, Methylparathion, Diazinon, Malathion, Lindane, Fenvalerate, Ethoprophos, Endrin, Endosulfan, Dimethoate, Dieldrin, Dicrotophos, Dichlorprop, Dichlorvos, Azinphos and its Derivatives, Aldrin, Disulfoton, Chlordimeform, Chlorpyrifos, Dicofol, Propargite, Demeton, Fipronil.

Herbicides, Fungicides or Plant growth Regulators may also be used. For example herbicides such as oxidiazon, anilofos, piperophos, esprocarb, benthiocarb, dimepiperate, molinate, pyributicarb, daimuron, butachlor, pretialchlor, butenochlor, terbuchlor, benzofenap, MCPCA (mapica) clomeprop, inabenfide, furyloxyfen, pyrazolynate, propanil, carbendazim, and fungicides such as triapenthenol, uniconazole, probenazole, validamycin, isoprothiolane, ediphenphos, tricyclazole, and iprobenfos.

Solvents which can be used in the invention are preferably liquid at room temperature (but, high temperature liquids may also be useful) and not miscible with water. They may be used as a single solvent or a mixture of solvents. Solvents which may be used include xylene, toluene, liquid alkyl substituted aromatic hydrocarbon; alkyl or alkenyl esters of aliphatic or aromatic acids, such as benzoates, salicylates or anthranilates, especially esters having 1 to 8 carbon atoms in the alcoholic part of the molecule and 6 to 18 carbon atoms in the acid part of the molecule; alkyl or aryl ethers; cyclohexanone vegetable oils such as cottonseed oil, soybean oil, corn off, rapeseed oil, coconut off, sunflower seed oil, olive oil, palm off, peanut off, safflower off, sesame off, rice bran off; esters derived from vegetable oils; vegetable oils are preferred as more environmentally friendly.

Cosolvents which may be used in the invention include ketones, like cyclohexanones; lactones like butyrolactone; amides; N-alkyl pyrrolidones, especially N-methyl-, N-octyl, N-decyl, and N-cyclohexyl-pyrrolidone; tetrahydrofuran, aliphatic or aromatic or heterocyclic substituted alcohols, such as tetrahydrofurfuryl alcohol.

Surface wetting spreaders (surfactant with dispersant properties) which can be used in the invention may be of any type compatible with the plant protecting agent, anionic or non-ionic or cationic or amphoteric surfactants. They include salts of lignosulphonic acids such as calcium lignosulfonate, salts of phenyl sulphonic or naphthalene sulphonic acids, condensed naphthalene sulfonic acid; poly condensates of ethylene oxide with fatty alcohols or fatty acids or fatty esters or fatty amines, or substituted phenols (particularly alkyphenols or arylphenols); salts of sulphosuccinic acid esters, such as sodium sulfosuccinate; taurine derivatives (particularly alkyltaurates); phosphoric esters of alcohols or of polycondensates of ethylene oxide with phenols; esters of polyols and of fatty acids or sulphuric acid or sulphonic acids or phosphoric acids; glyceryl esters, especially esters with fatty acids such as glyceryl stearate; substituted ethylene glycols; and the like.

Specific surface active agents which are advantageous which may further be added to the compositions of the invention are: dialkyl sulfosuccinates; alkylbenzene sulfonates salts, such as calcium dodecyl benzene sulfonate; ethoxylated tristyryl phenols, and sulfates and phosphates thereof; alkyl poylethoxyether phosphates esters, either in acid or in salt form; ethoxylated fatty acids or alcohols; ethoxylated alkyl phenols or dialkyl phenols; ethoxylated castor oil; ethoxylated propoxylated block copolymers; ethoxylated propoxylated alkylphenol block copolymers; ethoxylated propoxylated tristyrylphenols; glycerol esters, especially esters of fatty acids; glycol esters, especially esters of fatty acids; lecithin and lecithin derivatives; sugar esters and other derivatives, as sorbitol, and sucrose or glucose esters or derivatives; sucroglycerides.

Gelling agents which can be used in the invention are generally solid and have low solubility in the plant protecting composition and are able to form a homogeneous mixture as can be seen visually with the surface active agent of the plant protecting composition. Furthermore, the gelling agent is preferably also able to form a homogeneous, as can be seen visually, ternary mixture with the solvent and the surface active agent. It happens sometimes that the gelling agents are mixtures of different compounds which might not be gelling agents alone.

Gelling agents which can be advantageously used are: polyacrylic derivatives such as polyacrylic salts, especially the alkali or ammonium salts; sodium dioctyl sulfosuccinate, optionally mixed with organic salts, such as sodium benzoate; silica; sodium acetate in combination with other compounds; urea; alumina; titanium dioxide; sugars; lignosulfonates; salts of alkyl arylsulfonates, such as sodium dodecyl benzene sulfonate; combinations of modified clay and propylene carbonate; hydrogenated castor oil; ethoxylated vegetable oil; tetramethyl decynediol; mixtures of dimethyl hexane diol and hexyne diol; and mixtures thereof. Some gelling agents might have both an surface acting action and a gelling action such as ethoxylated/propoxylated alkyl phenol block copolymers; ethoxylated alkyl phenols and dialkyl phenols; ethoxylated fatty acids; ethoxylated fatty alcohols; ethoxylated propoxylated block copolymers; and mixtures thereof.

The gel material which is used in the invention is essentially a material which has a phase difference phi between the controlled shear stress and the resulting shear strain such that Tg(phi) is less than or equal to 1.5. Tg(phi) is the tangent of the phi angle (or phase difference). The measurement of phi is made by means of a dynamic rheometer. Dynamic rheometers which are appropriate to measure phi are known and available commercially. They usually have a flat fixed plate and a rotating cone or plate, or a so-called couette measuring system. Other mechanical systems are also available. Generally the choice of one system or another is made according to the recommendations of the seller of the rheometer, and is adapted to the kind of compound, gel or liquid, which is tested. The particular choice of a specific type of rheometer is something well known by the man skilled in the art of rheology. A rotating plate over another plate or a cone rotating over a plate are often more appropriate when a gel or a viscous liquid is tested. When two kinds of system for the rheometer are possible, similar values of phi are actually measured. The cone (or the plate or the couette) is caused to rotate by means of a controlled speed motor; the rotation is a sinusoidal one, i.e., the strain and the angular displacement change as a sine function with time. Tg(phi) is equal to the ratio G''/G', wherein: G' is the storage modulus (represents the behavior of a perfect solid); G'' is the loss modulus (represents the behavior of a perfect liquid). G' and G'' are expressed in Pascal for a given rotational speed (radian per second).

G' and G'', and thus Tg(phi), may depend on the amplitude of the oscillations (percentage of strain) of the rheometer; however, there is generally a so-called viscoelastic plateau whereby the values G' and G'' of a gel do not depend substantially on the said amplitude; this means that in the conditions of the test under the viscoelastic plateau the structure of the gel is maintained and no destruction of the gel into a liquid happens. Of course, the measurement of G' and G'' of a gel is made under the conditions of this viscoelastic plateau, just because it corresponds to the normal gel structure which is precisely what is tested.

G' and G'', and thus Tg(phi), may also depend on the speed of the oscillations (time to reach the chosen percentage of strain; expressed as radian per second) of the rheometer; however, when the gel is well structured, there is no so much variation from one speed to another. In order to have a reasonable measurement of the properties of a gel, it is generally preferred to operate in conditions whereby the gel is not too much stressed, that is to say at speed such as 1 rd/s. Of course, measurements at higher speed may also be made.

As already stated, the plant protecting unit comprise a plant protecting composition contained in a water soluble envelope, the said composition comprising a plant protecting active ingredient and a solvent and at least one gelling agent and at least one surface active and optionally, but preferably, a sticker and/or a spreader.

The amount of active ingredient in the plant protecting composition of the invention is generally comprised between 0.1 and 60% of the total plant protecting composition contained in the envelope, preferably between 1 and 40% (in the present specification, unless otherwise specified, the percentage are w/w).

The amount of solvent in the plant protecting composition of the invention is generally comprised between 10 and 95% of the total plant protecting composition contained in the envelope, preferably between 30 and 90%.

The amount of surface active agent (wetting spreader) in the plant protecting composition of the invention is generally comprised between 0.5 and 30% of the total plant protecting composition contained in the envelope, preferably between 0.8 and 20%.

The amount of gelling agent in the plant protecting composition of the invention is generally comprised between 0.1 and 20% of the total plant protecting composition contained in the envelope, preferably between 0.3 and 10%.

The amount of sticker in the plant protecting composition of the invention, if any, is generally comprised between 0.0% and 20% of the total plant protecting composition contained in the envelope, preferably between 0.5% and 20%, more preferably between 0.5 and 10%.

The following examples are given to illustrate the inventions and some mode of realization. It is not intended to restrict the invention to these particular examples. One of ordinary skill in the art could select solvents, gelling agents, films and the like.

EXAMPLE 1

An insecticidal composition was made by attrition grinding of a mixture off:

1.33% of a 1-haloaryl 3-CN pyrazole whose water solubility is 3 mg/liter at 20° C.
85.1% of corn oil which is immiscible with water
5% of N-Methyl-pyrrolidone

6% of alphadecyl omegahydroxy hexaethoxylated decylalcohol which is a wetting agent 2.5% of sodium dioctyl sulfosuccinate mixed with sodium benzoate 0.07% of a tracer dye The Brookfield viscosity was 3000 cps; the density was 0.929 g/$cm^3$.

This composition was put in a polyvinyl alcohol water soluble envelope which was closed by heat sealing.

10 similar envelopes are dropped onto a rectangular paddy comprising 10 sub-rectangles of 10 $m^2$ each. One envelope is dropped on each sub-rectangle. The envelope dissolves in less than 3 minutes. The composition spreads in 30 minutes covering over the whole paddy and sticks to the stem.

The insecticidal effect, as determined six days after treatment by measurement of the percentage of plants damaged by rice water weevil, was 6.6%.

I claim:

1. A method for the treatment of growing paddy rice in a water containing paddy comprising positioning in the water, at least one 10 to 1500 ml cold water soluble polymeric sealed envelope enclosing therein a plant protecting composition in the form of a viscous or sticky fluid or a viscous or sticky gel having a specific gravity less than 1 g/$cm^3$ that will spread or rapidly form a uniform film along the surface of the water surrounding the envelope and will coat rice plants in response to changes in water level in the rice paddy wherein the wall of the envelope has a thickness of 10 micrometers to 1 millimeter wherein the fluid or gel comprises between 10 and 95% solvent between 0.1 to 60% of active ingredient and between 0.5 and 30% surfactant and wherein the active ingredient has solvent/solubility in water greater than 5.

2. The method according to claim 1 wherein the active ingredient is a plant growth regulator or a pesticide.

3. The method according to claim 1 wherein the active ingredient is selected from the group consisting of an insecticide, a fungicide, or a herbicide, a nematicide, a miticide and a molluscicide.

4. The method according to claim 1 which is applied for control of insects which move or travel along rice plant stems.

5. The method according to claim 3 wherein the insecticide will control rice water weevil, rice stem borer, grass leaf roller, rice leaf beetle or brown plant hopper.

6. The method according to claim 1 wherein a plurality of envelopes are dropped onto the water in spaced relationship such that the plant protecting composition from each of the envelopes join to form a film over essentially the whole surface of the water of the paddy.

7. The method according to claim 1 wherein the plant protecting composition has a water solubility less than 0.1% (w/w).

8. The method according to claim 1 wherein the water soluble envelope floats on the surface of the water.

9. The method according to claim 1 wherein the plant protection composition is a fluid.

10. The method according to claim 1 wherein the plant protection composition is a gel.

11. The method according to claim 1 wherein the fluid or gel comprises a cosolvent, a wetting spreader or a cosolvent and a wetting spreader.

12. The method according to claim 1 wherein the fluid or gel comprises a vegetable oil.

13. The method according to claim 1 wherein the fluid or gel comprises a vegetable oil selected from the group consisting of cotton seed oil, soybean oil, corn oil, rapeseed oil, sunflower seed oil, and coconut oil.

14. The method according to claim 1 wherein the plant protecting composition does not flow through pinholes and has a tangent of the phase angle between shear stress and shear strain is less than 1.5.

15. The method according to claim 1 wherein the solvent is selected from the group consisting of liquid alkyl substituted aromatic hydrocarbons, alkyl or alkenyl esters of aliphatic or aromatic acids, cyclohexanone, esters having 1 to 8 carbon atoms in the alcoholic part of the molecule and 6 to 8 carbon atoms in the acid part of the molecule alkyl or aryl ethers, vegetable oils, and esters derived from vegetable oils.

16. The method according to claim 1 wherein the fluid or gel further comprises a cosolvent selected from the group consisting of ketones, lactones, amides, tetrahydrofurane, and aliphatic or aromatic of heterocyclic substituted alcohols.

17. A method according to claim 1 wherein the gel further comprises a gelling agent.

18. A method according to claim 1 further comprising lowering the level of water in the paddy after said treatment such that a portion of stems of the rice plants are coated with the plant protecting composition.

19. A method according to claim 1 wherein the fluid or gel further comprises a sticker from about 20% or less of the plant protecting composition.

20. A method according to claim 19 wherein the sticker is from about 0.5% and about 10% of the fluid or gel.

* * * * *